(12) United States Patent
Paxon et al.

(10) Patent No.: US 8,440,469 B2
(45) Date of Patent: May 14, 2013

(54) SYSTEM AND METHOD FOR INCREASING SPECTROSCOPIC SIGNAL

(75) Inventors: Tracy Lynn Paxon, Waterford, NY (US); Frank John Mondello, Niskayuna, NY (US); Yuan-Hsiang Lee, Winchester, MA (US); Michael Craig Burrell, Clifton Park, NY (US)

(73) Assignee: Morpho Detection, Inc., Newark, CA (US)

( * ) Notice: Subject to any disclaimer, the term of this patent is extended or adjusted under 35 U.S.C. 154(b) by 849 days.

(21) Appl. No.: 11/764,537

(22) Filed: Jun. 18, 2007

(65) Prior Publication Data

US 2008/0309335 A1 Dec. 18, 2008

(51) Int. Cl.
*G01N 33/553* (2006.01)
*G01N 33/543* (2006.01)

(52) U.S. Cl.
USPC .............................. 436/526; 436/518; 436/525

(58) Field of Classification Search .................. 436/526, 436/518, 525
See application file for complete search history.

(56) References Cited

U.S. PATENT DOCUMENTS

| | | | |
|---|---|---|---|
| 5,445,971 A * | 8/1995 | Rohr | 436/526 |
| 5,458,785 A | 10/1995 | Howe et al. | |
| 5,897,783 A | 4/1999 | Howe et al. | |
| 5,976,369 A | 11/1999 | Howe et al. | |
| 6,764,959 B2 * | 7/2004 | Yu et al. | 438/762 |
| 2006/0240572 A1 | 10/2006 | Carron et al. | |
| 2008/0160634 A1 * | 7/2008 | Su et al. | 436/501 |

* cited by examiner

*Primary Examiner* — Mark Shibuya
*Assistant Examiner* — Pensee Do
(74) *Attorney, Agent, or Firm* — Armstrong Teasdale LLP

(57) ABSTRACT

A method for increasing a spectroscopic signal in a biological assay is provided. The method includes forming a suspension of magnetically attractable particles. The method also includes introducing a first magnetic field at a first location to draw the magnetically attractable particles towards the first location and form a first agglomeration. The method also includes removing the first magnetic field. The method further includes introducing a second magnetic field at a second location to draw the first agglomeration towards the second location and form a second agglomeration. The method further includes focusing an excitation source on the second agglomeration formed at the second location.

13 Claims, 4 Drawing Sheets

SYSTEM AND METHOD FOR INCREASING SPECTROSCOPIC SIGNAL

BACKGROUND

The invention relates generally to assay systems and more specifically to biological assay systems.

Magnetic separation is a technique that is widely used for the purification or quantification of biological molecules, specific proteins, cells and nucleic acids. An advantage of this technique is that it provides rapid separation while applying minimal mechanical stress on an analyte. The technique is also simple, inexpensive and highly scalable. Further, techniques employing magnetism are amenable to automation and miniaturization.

The magnetic separation technique employs magnetically attractable particles for separation of specific targets from a liquid. The magnetically attractable particles are suspended in the liquid containing targets of interest in an impure or dilute form. The targets are captured by the magnetically attractable particles via a binding mechanism (for example, antibody antigen binding). Further, a magnetic field is applied to a container filled with the liquid causing the particles to migrate towards the field along with the bound targets and forming a pellet. While the magnetic field is still applied, remaining liquid may be discarded leaving the pellet intact. An example of such a technique may be found in U.S. patent application publication number 2006/0216697, assigned to the assignee of the present application.

SUMMARY

In accordance with an aspect of the invention, a method for increasing a spectroscopic signal in a biological assay is provided. The method includes forming a suspension of magnetically attractable particles. The method also includes introducing a first magnetic field at a first location to attract the magnetically attractable particles towards the first location and form a first agglomeration. The method also includes removing the first magnetic field and introducing a second magnetic field at a second location to attract the first agglomeration towards the second location and form a second agglomeration. The method further includes focusing an excitation source on the second agglomeration formed at the second location.

In accordance with another aspect of the invention, a system for enhancing a spectroscopic signal is provided. The system includes a container including a plurality of pathogens including at least one strain of pathogens. The container also includes a plurality of magnetic beads and a plurality of tags, each of the magnetic beads and the tags being configured to attach to the same strain of the pathogen. The system also includes at least one magnet configured to induce a first magnetic field in proximity of a first location of the container and form a first agglomeration of pathogens, magnetic beads and tags. The system also includes a second magnetic field in proximity of a second location of the container for creating a second agglomeration from the first agglomeration. The system further includes an excitation source configured to generate a spectroscopic signal indicative of a quantity of the plurality of pathogens in the container.

These and other features, aspects, and advantages of the invention will become better understood when the following detailed description is read with reference to the accompanying drawings.

DETAILED DESCRIPTION OF EXEMPLARY EMBODIMENTS

As discussed in detail below, embodiments of the invention include a system and method for increasing spectroscopic signal in a biological assay system. Non-limiting examples of the type of spectroscopy used herein are Raman, surface-enhanced Raman, resonance Raman, and surface-enhanced resonance Raman spectroscopy.

Figure 1:
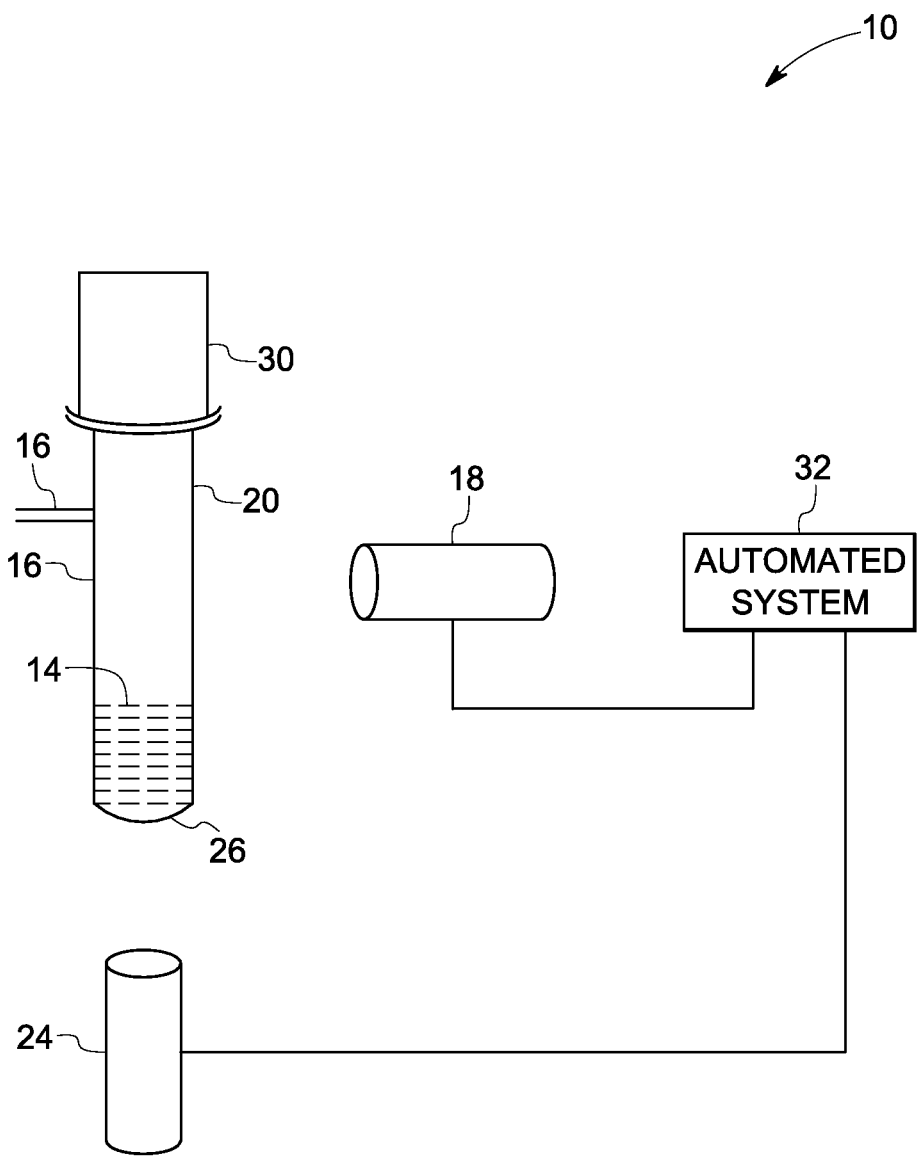
FIG. 1 is a schematic illustration of a biological assay system utilizing magnetism in accordance with an embodiment of the invention.

FIG. 1 is a schematic illustration of a biological assay system 10 utilizing magnetism. The biological assay system 10 includes a container or tube 12 containing a fluid 14. A mechanical attachment 16 provides a means for a holder to fix the container 12 at a desired position. The mechanical attachment 16 may be, for example, a clamp, tube, or pellet-forming device. A first magnet 18 may be positioned at a first location of the container 12 and configured to induce a first magnetic field in proximity of the first location. In an exemplary embodiment, the first location is at a side 20 of the container 12 at a location between the bottom of the tube and top level of the fluid. Similarly, a second magnet 24 may be positioned at a second location of the container 12 to induce a second magnetic field in proximity of the second location. As shown in FIG. 1, the second location is at a bottom 26 of the container 12. In an exemplary embodiment, the first location and the second location may be on a same side of the container 12. In another exemplary embodiment, at least one of the first magnet 18 and the second magnet 24 are toroidal in shape. An agglomeration (not shown) of a biological system including multiple pathogens and multiple magnetic beads is formed and suspended within the container 12 due to the induced magnetic field. The container 12 further includes a cap 30 to provide a tight seal. In a particular embodiment, an automated system 32 may be coupled to at least one of the first magnet 18 and the second magnet 24 for automated movement.

Figure 2:
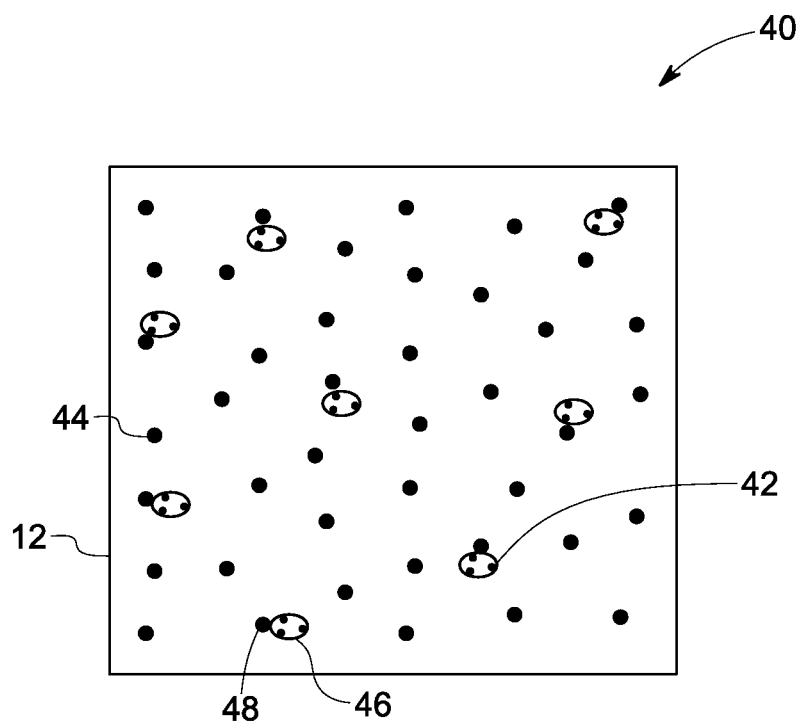
FIG. 2 is a schematic illustration of the assay suspension in FIG. 1.

FIG. 2 is a schematic illustration of an exemplary biological system 40 suspended in the container 12 in FIG. 1. The biological system 40 includes multiple pathogens 42 including at least one strain of pathogens. As used herein, the term 'strain' refers to a subtype of a virus or a bacterium or other biological material. Multiple unbound magnetic beads 44 and multiple tags 46 are suspended in the container 12 and configured to attach to a same strain of the pathogen 42 to form a complex or an agglomeration. The pathogens 42 that attach to tags 46 are referred to as tagged pathogens. Similarly, the magnetic beads 44 that bind to the tagged pathogens are referred to as bound magnetic beads 48. Some non-limiting examples of the tags 46 include surface-enhanced Raman spectroscopy tags, surface-enhanced resonant Raman spectroscopy tags, fluorescent labels, or colorimetric tags.

In a particular embodiment, tags 46 include target-binding moieties including, but not limited to, antibodies, aptamers, polypeptides, nucleic acid, peptide nucleic acids, avidin, streptavidin, and derivatives of avidin and streptavidin. A Raman-active tag may include one target-binding moiety or a plurality of target-binding moieties. The plurality of target-binding moieties may all be of the same kind of target-binding moieties or different kinds of target-binding moieties. The target-binding moieties may also be of differing kinds capable of attaching to different types of pathogens. The target-binding moieties may attach to the pathogens 42, directly or indirectly. Some non-limiting examples of attaching include, but are not restricted to, electrostatically, chemically, and physically.

The pathogens 42 may include living targets and non-living targets. The targets may include a disease producing biological molecule. Some non-limiting examples of targets include prokaryotic cells, eukaryotic cells, bacteria, spores, viruses, proteins, polypeptides, toxins, liposomes, beads, ligands, amino acids, and nucleic acids, either individually or in any combinations thereof. The targets may include extracts of the above living or non-living targets.

Examples of prokaryotic cells include, but are not limited to, bacteria also include extracts thereof. Examples of eukaryotic cells include, but are not limited to, yeast cells, animal cells and tissues. Non-limiting examples of beads include, but are not limited to, latex, polystyrene, silica and plastic.

In a particular embodiment, the magnetic beads 44 include nano or micron sized superparamagnetic beads that are attracted by a magnetic field but retain little or no residual magnetism when the field is removed. Examples of superparamagnetic beads include, but are not limited to, iron oxides such as magnetite.

Figure 3:
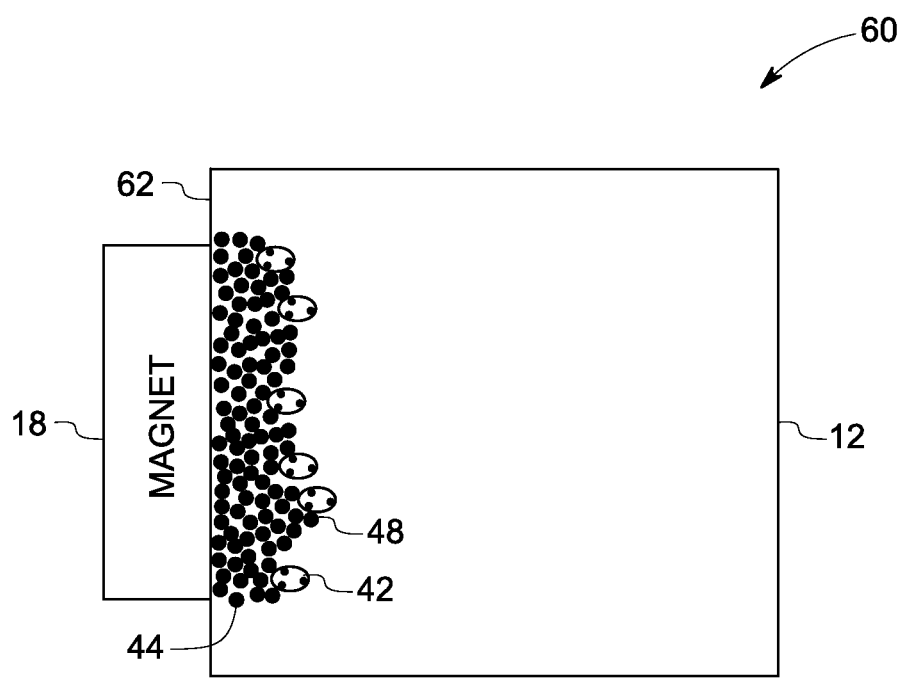
FIG. 3 is a schematic illustration of an agglomeration formed at a side of the container of FIG. 1.

FIG. 3 is a schematic illustration of a biological assay system 60 with a first magnet 18, as referenced in FIG. 1, disposed in proximity of a first location of the container 12. As shown in FIG. 3, the first location is at a side 62 of the container 12. The first magnet 18 introduces a first magnetic field that draws unbound magnetic beads 44 toward the side 62. Similarly, the bound magnetic beads 48 including the tagged pathogens 42 migrate toward the side 62. Through such migration, unbound magnetic beads 44 presumably become positioned closer to the magnet 18 than the bound magnetic beads 48 and tagged pathogens 42.

Figure 4:
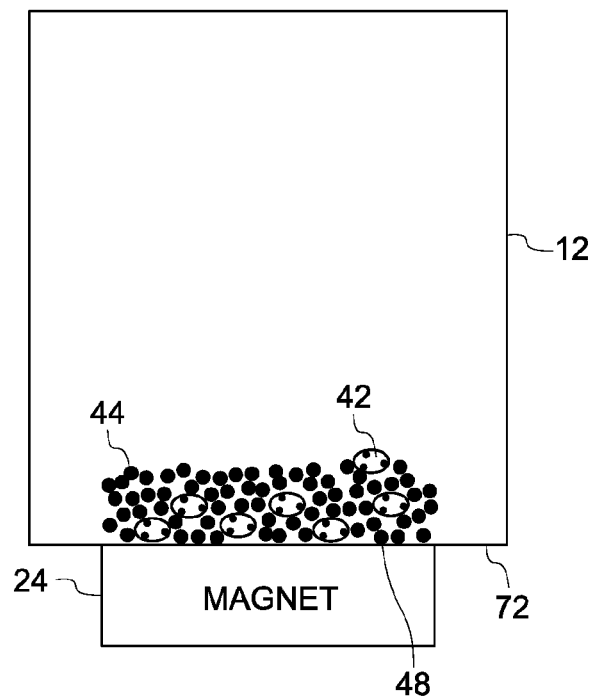
FIG. 4 is a schematic illustration of an agglomeration formed at a bottom of a container in accordance with an embodiment of the invention.

FIG. 4 is a schematic illustration of the biological assay system 60 with a second magnet 24, as referenced in FIG. 1, disposed in proximity of a second location of the container 12. As shown in FIG. 4, the second location is at a bottom 72 of the container 12. The first magnet 18 is removed to a distance where a force on the unbound magnetic beads 44 and the bound magnetic beads 48 is negligible. The second magnet 24 further introduces a second magnetic field that draws first the bound magnetic beads 48 including the tagged pathogens 42 towards the bottom 72. Similarly, the unbound magnetic beads 44 migrate towards the bottom 72. In an alternative embodiment, the first magnet 18 may not be removed, but instead a second magnet 24 may be introduced having a second magnetic field that has sufficient strength to draw the bound magnetic beads 48 including the tagged pathogens 42 and the unbound magnetic beads 44. Due to the initial positioning of the unbound magnetic beads 44 and the bound magnetic beads 48 and the tagged pathogens 42, there is a time lag between the time the tagged pathogens 42 arrive at the bottom 72 and the time the unbound magnetic beads 44 arrive at the bottom 72. The tagged pathogens 42 are further away from the side 62 and closer to the bottom 72 as compared to the unbound magnetic beads 44 when the second magnetic field is introduced. Presumably, the tagged pathogens 42 have a shorter distance to travel, enabling them generally to arrive at the bottom 72 before the unbound magnetic beads 44. This results in a greater density of tagged pathogens 42 closer to the bottom 72.

Figure 5:
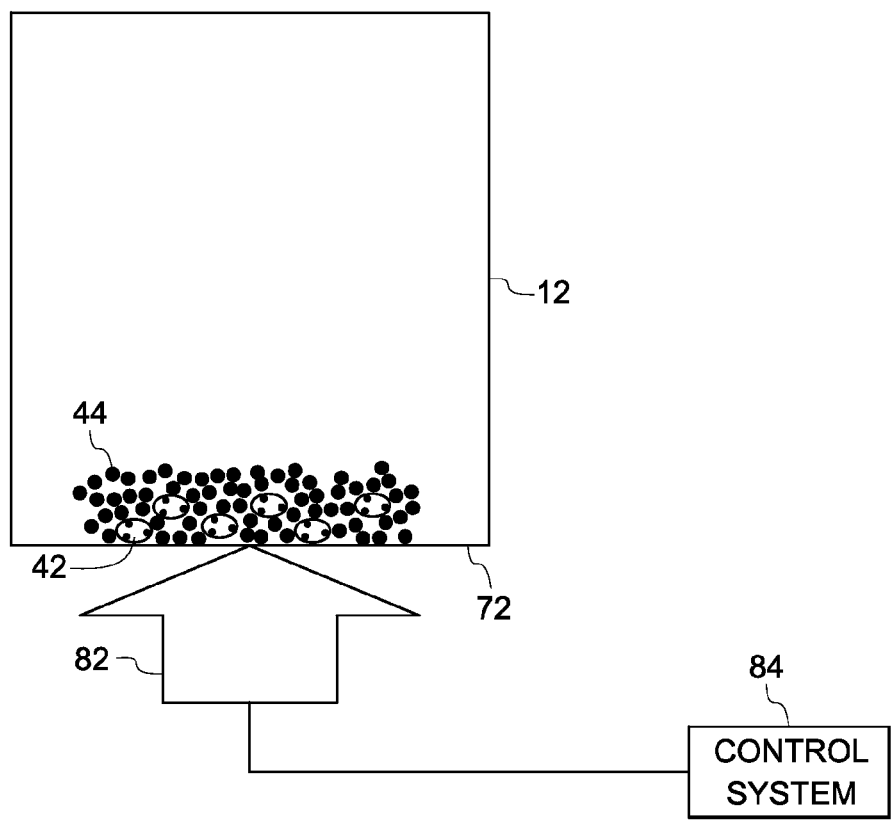
FIG. 5 is a schematic illustration of a capture of a spectroscopic signal at the bottom of the container by an excitation source.

FIG. 5 is a schematic illustration of the biological assay system 60 including an excitation source 82 to measure spectroscopy. The excitation source 82 is disposed at the second location wherein the second magnetic field was introduced, such as a bottom 72 as in the present illustration. However, the second location may be any location apart from the first location on a surface of the container 12. In a particular embodiment, the excitation source 82 includes a monochromatic source of light such as, but not limited to, a monochromatic laser. The excitation source 82 is electrically coupled to a control system 84 to output a spectroscopic signal. Due to the greater density of tagged pathogens 42 closer to the excitation source 82, an enhanced signal to noise ratio can be obtained in the spectroscopic signal. In a particular embodiment, the signal to noise ratio is noticeably improved.

Figure 6:
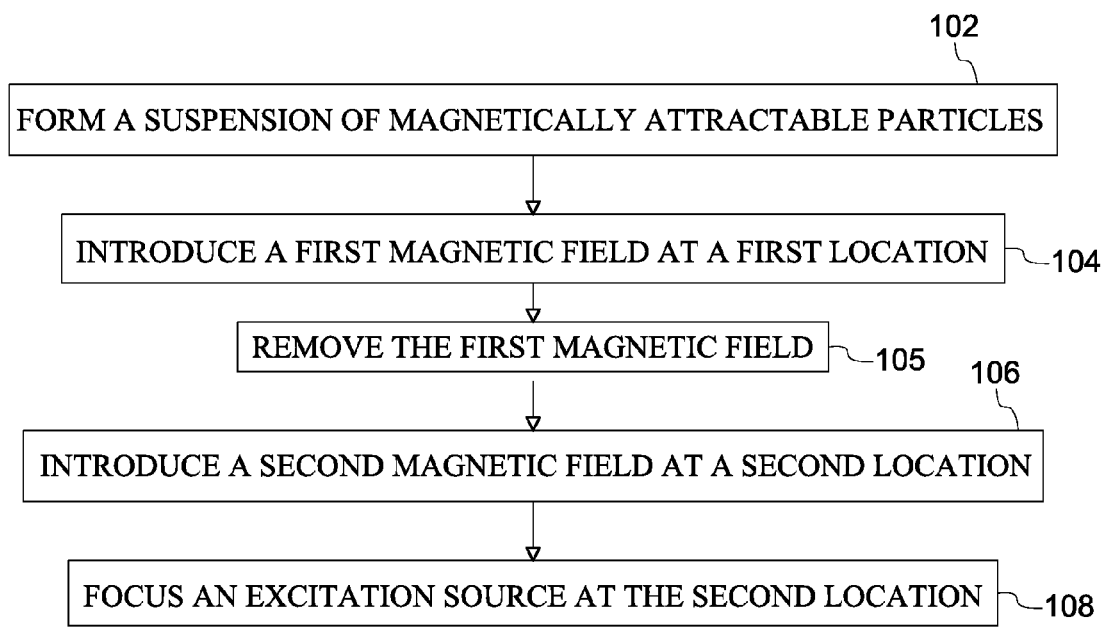
FIG. 6 illustrates process steps involved in increasing spectroscopic signal in a biological assay system in accordance with an embodiment of the invention.

FIG. 6 is a flow chart illustrating process steps involved in increasing spectroscopic signal in a biological assay system. The process includes forming a suspension of magnetically attractable particles in step 102. In a particular embodiment, the suspension is formed via a tagging mechanism. A first magnetic field is introduced at a first location to draw the magnetically attractable particles toward a first location and form a first agglomeration in step 104. In a particular embodiment, a first magnet is disposed near the first location to introduce the first magnetic field. Further, after removal of the first magnetic field in step 105, a second magnetic field is introduced at a second location to draw the first agglomeration toward the second location and form a second agglomeration in step 106. In a particular embodiment, a second magnet is disposed near the second location to introduce the second magnetic field. An excitation source is focused on the second agglomeration formed at the second location in step 108. In an embodiment, a monochromatic laser is focused. In an exemplary embodiment, a control system is coupled to the excitation source to output a spectroscopic signal.

The various embodiments of a system and method for enhancing spectroscopic signal in a biological assay system provide a way to achieve a convenient and efficient means of biodetection. These techniques also allow for highly efficient security systems due to improved detection.

Of course, it is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the use of a first magnet to induce a magnetic field near a wall of a container with respect to one embodiment can be adapted for use with a second magnet to induce a magnetic field near the same wall described with respect to another. Similarly, the various features described, as well as other known equivalents for each feature, can be mixed and matched by one of ordinary skill in this art to construct additional systems and techniques in accordance with principles of this disclosure.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for increasing a spectroscopic signal in a biological assay, said method comprising:

suspending a plurality of magnetically-attractable particles and a plurality of pathogens including at least one strain of pathogen in a container;

forming a suspension that includes a plurality of bound magnetically-attractable particles that are each bound to a pathogen of the plurality of pathogens and a plurality of unbound magnetically-attractable particles that are each not bound to any pathogens of the plurality of pathogens;

introducing a first magnetic field at a first location to attract the plurality of bound magnetically-attractable particles and the plurality of unbound magnetically-attractable particles of the suspension toward the first location and form a first agglomeration having a first configuration that includes a first density of bound magnetically-attractable particles positioned near the first location;

introducing a second magnetic field at a second location to attract the plurality of bound magnetically-attractable particles and the plurality of unbound magnetically-attractable particles of the suspension toward the second location and form a second agglomeration having a second configuration that is different from the first configuration, the second configuration having a second density of bound magnetically-attractable particles positioned near the second location that is greater than the first density near the first location, the second density configured to enhance a signal-to-noise ratio for increasing a spectroscopic signal; and focusing an excitation source on the second agglomeration formed at the second location to generate the spectroscopic signal.

2. A method in accordance with claim 1, wherein said forming comprises forming the suspension via a tagging mechanism.

3. A method in accordance with claim 1, further comprising electrically coupling a control system to the excitation source to output a spectroscopic signal.

4. A method in accordance with claim 1, wherein said focusing an excitation source comprises focusing a monochromatic laser on the second agglomeration.

5. A method in accordance with claim 1, wherein said introducing a first magnetic field comprises disposing a first magnet near the first location.

6. A method in accordance with claim 1, wherein said introducing a second magnetic field comprises disposing a second magnet near the second location.

7. A method in accordance with claim 1, further comprising forming the first agglomeration having the first configuration to include the plurality of unbound magnetically-attractable particles positioned nearer the first magnetic field than the plurality of pathogens.

8. A method in accordance with claim 7, further comprising forming the second agglomeration having the second configuration to include at least one pathogen of the plurality of pathogens positioned nearer the second magnetic field than the unbound magnetically-attractable particles are to the second magnetic field.

9. A method in accordance with claim 1, further comprising forming the suspension to include at least one tag coupled to a corresponding pathogen of the plurality of pathogens to form a tagged pathogen.

10. A method in accordance with claim 1, further comprising forming the suspension in a tube.

11. A method in accordance with claim 10, further comprising introducing a first magnetic field at a side of the tube.

12. A method in accordance with claim 11, further comprising introducing a second magnetic field at a bottom of the tube.

13. A method in accordance with claim 1, further comprising removing the first magnetic field before the second magnetic field is introduced.

* * * * *